United States Patent
Bramlet et al.

(10) Patent No.: US 6,447,546 B1
(45) Date of Patent: Sep. 10, 2002

(54) APPARATUS AND METHOD FOR FUSING OPPOSING SPINAL VERTEBRAE

(75) Inventors: Dale G. Bramlet, 2044 Brightwaters Blvd., NE., St. Petersburg, FL (US) 33704-3010; Peter Sterghos, St. Petersburg, FL (US); Jeffrey W. Godsted, Round Rock, TX (US)

(73) Assignee: Dale G. Bramlet, St. Petersburg, FL (US)

( * ) Notice: Subject to any disclaimer, the term of this patent is extended or adjusted under 35 U.S.C. 154(b) by 27 days.

(21) Appl. No.: 09/635,436

(22) Filed: Aug. 11, 2000

(51) Int. Cl.[7] .................................................. A61F 2/44

(52) U.S. Cl. .............................. 623/17.16; 623/17.11

(58) Field of Search ........................... 623/17.11, 17.12, 623/17.13, 17.14, 17.15, 17.16, 17.17, 16.11; 606/61

(56) References Cited

U.S. PATENT DOCUMENTS

| | | | |
|---|---|---|---|
| 3,374,786 A | | 3/1968 | Callender, Jr. ................ 128/92 |
| 3,791,380 A | * | 2/1974 | Dawidowski ................. 128/92 |
| 3,892,232 A | | 7/1975 | Neufeld ........................ 128/92 |
| 4,009,712 A | | 3/1977 | Burstein et al. .............. 128/92 |
| 4,175,555 A | | 11/1979 | Herbert ......................... 128/92 |
| 4,237,875 A | | 12/1980 | Termanini ..................... 128/92 |
| 4,379,451 A | | 4/1983 | Getscher ....................... 128/92 |
| 4,409,974 A | | 10/1983 | Freedland ...................... 128/92 |
| 4,432,358 A | | 2/1984 | Fixel ............................. 128/92 |
| 4,488,543 A | | 12/1984 | Tornier .......................... 128/92 |
| 4,494,535 A | | 1/1985 | Haig .............................. 128/92 |
| 4,519,100 A | | 5/1985 | Wills et al. ..................... 3/1.9 |
| 4,561,432 A | | 12/1985 | Mazor ........................... 128/92 |
| 4,612,920 A | | 9/1986 | Lower ........................... 128/92 |
| 4,621,629 A | | 11/1986 | Koeneman ..................... 128/92 |
| 4,632,101 A | | 12/1986 | Freedland ..................... 128/92 |
| 4,653,489 A | | 3/1987 | Tronzo ......................... 128/92 |
| 4,657,001 A | | 4/1987 | Fixel ............................. 128/92 |
| 4,721,103 A | | 1/1988 | Freedland ..................... 128/92 |
| 4,759,352 A | | 7/1988 | Loxier ........................... 128/92 |
| 4,787,378 A | | 11/1988 | Sodhi ............................ 128/92 |
| 4,791,918 A | | 12/1988 | Von Hasselbach .......... 128/924 |
| 4,898,156 A | | 2/1990 | Gatturna et al. ............... 606/72 |
| 4,946,468 A | | 8/1990 | Li ................................ 606/232 |
| 4,964,403 A | | 10/1990 | Karas et al. .................... 606/60 |
| 4,968,315 A | | 11/1990 | Gatturna ....................... 606/72 |
| 4,969,887 A | | 11/1990 | Sodhi ............................ 606/67 |

(List continued on next page.)

FOREIGN PATENT DOCUMENTS

| | | |
|---|---|---|
| EP | 0 637 439 | 2/1995 |
| EP | 0 697 200 | 2/1996 |
| EP | 0 951 879 | 10/1999 |

OTHER PUBLICATIONS

"Anchorlok™ Questus™ Leading Edge™ Soft Tissue Anchor System," Brochure, Wright Medical Technology, Inc., 1995.

Primary Examiner—Corrine McDermott
Assistant Examiner—Hieu Phan
(74) Attorney, Agent, or Firm—Kenyon & Kenyon

(57) ABSTRACT

An apparatus and method for fusing opposing spinal vertebrae is disclosed. In an embodiment for a spinal implant of the present invention, the implant includes a body assembly and a retention member coupled to the body assembly. The retention member includes a tang where the tang is extendible from the body assembly. In a method of the present invention, the method includes the step of inserting an implant between adjacent vertebrae with a retention member of the implant in a first retracted configuration. The method also includes the step of configuring the retention member in a second extended configuration wherein when the retention member is in its second extended configuration, a portion of a tang of the retention member extends from the implant and into one of the adjacent vertebrae.

21 Claims, 12 Drawing Sheets

U.S. PATENT DOCUMENTS

| | | | |
|---|---|---|---|
| 4,973,332 A | 11/1990 | Kummer | 606/65 |
| 4,973,333 A | 11/1990 | Treharne | 606/77 |
| 5,002,550 A | 3/1991 | Li | 606/139 |
| 5,007,910 A | 4/1991 | Anapliotis et al. | 606/65 |
| 5,032,125 A | 7/1991 | Durham et al. | 606/62 |
| 5,041,114 A | 8/1991 | Chapman et al. | 606/62 |
| 5,041,116 A | 8/1991 | Wilson | 606/65 |
| 5,046,513 A | 9/1991 | Gatturna et al. | 128/898 |
| 5,057,103 A | 10/1991 | Davis | 606/63 |
| 5,062,851 A | 11/1991 | Branemark | 623/18 |
| 5,087,266 A | 2/1992 | Fixel | 606/65 |
| 5,098,433 A | 3/1992 | Freedland | 606/63 |
| 5,116,336 A | 5/1992 | Frigg | 606/65 |
| 5,129,901 A | 7/1992 | Decoste | 606/65 |
| 5,176,681 A | 1/1993 | Lawes et al. | 606/64 |
| 5,192,303 A | 3/1993 | Gatturna et al. | 606/232 |
| 5,207,679 A | 5/1993 | Li | 606/72 |
| 5,217,486 A | 6/1993 | Rice et al. | 606/232 |
| 5,300,074 A | 4/1994 | Frigg | 128/67 |
| 5,324,292 A | 6/1994 | Meyers | 606/73 |
| 5,356,410 A | 10/1994 | Pennig | 606/62 |
| 5,356,413 A | 10/1994 | Martins et al. | 606/75 |
| 5,372,599 A | 12/1994 | Martins | 606/75 |
| 5,417,692 A | 5/1995 | Goble et al. | 606/73 |
| 5,417,712 A | 5/1995 | Whittaker et al. | 606/232 |
| 5,429,641 A | 7/1995 | Gotfried | 606/67 |
| 5,437,674 A | 8/1995 | Worcel et al. | 606/73 |
| 5,456,721 A | 10/1995 | Legrand | 623/13 |
| 5,458,601 A | 10/1995 | Young, Jr. et al. | 606/72 |
| 5,472,452 A | 12/1995 | Trott | 606/232 |
| 5,478,342 A | 12/1995 | Kohrs | 606/73 |
| 5,489,210 A | 2/1996 | Hanosh | 433/173 |
| 5,522,845 A | 6/1996 | Wenstrom, Jr. | 606/232 |
| 5,531,792 A | 7/1996 | Huene | 623/16 |
| 5,534,004 A | 7/1996 | Santangelo | 606/68 |
| 5,571,104 A | 11/1996 | Li | 606/72 |
| 5,578,035 A | 11/1996 | Lin | 606/68 |
| 5,591,168 A | 1/1997 | Judet et al. | 606/65 |
| 5,593,409 A | 1/1997 | Michelson | 606/61 |
| 5,643,321 A | 7/1997 | McDevitt | 606/232 |
| 5,702,449 A | 12/1997 | McKay | 623/17 |
| 5,766,253 A | 6/1998 | Brosnahan, III | 623/17 |
| 5,800,550 A * | 9/1998 | Sertich | 623/17 |
| 5,895,427 A | 4/1999 | Kuslich et al. | 623/17 |
| 5,968,098 A | 10/1999 | Winslow | 623/17 |
| 5,980,522 A * | 11/1999 | Koros et al. | 606/61 |
| 6,129,763 A * | 10/2000 | Chauvin et al. | 623/17 |
| 6,214,050 B1 * | 4/2001 | Huene | 623/17.15 |

* cited by examiner

APPARATUS AND METHOD FOR FUSING OPPOSING SPINAL VERTEBRAE

BACKGROUND OF THE INVENTION

1. Field of the Invention

The present invention relates to an implant for use in surgical procedures for fusing adjacent bone structures and more specifically adjacent vertebrae.

2. Description of the Related Art

The fusion of adjacent bone structure is commonly performed to provide for long-term replacement to compensate for degenerative and or deteriorated disorders in bone. In many cases, low back pain can be avoided by preventing relative motion between spinal vertebrae. By fusing the contiguous vertebrae in the lumbar region, lower back pain can be abated.

Surgical techniques are known for use in spinal stabilization. Surgical techniques seek to rigidly join the vertebrae that are separated by a degenerated disk. Ideally, the surgery effectively replaces the vertebra-disk-vertebra combination with a single rigid vertebra. Various surgical techniques have been developed to approximate this ideal.

Many of the techniques begin by partially removing the degenerative disk material. Where the techniques differ is in their strategy for replacing the disc material. Some procedures fill the void left between the contiguous vertebra with bone graft. Other techniques rely on the use of an implant acting alone or in combination with bone fragments. Usually, initial stabilization is achieved by making the implant diameter slightly larger than the void between the vertebrae. Eventual fusion of the opposing bone segments results from bone growth into and through the implant.

In some cases, the above procedures have failed due to shifting of the implant between the adjacent vertebrae during the initial stabilization period, i.e., prior to fusion taking place. This translation of the implant can lead to discomfort and serious consequences for the patient due to the proximity of nerves and blood vessels in the implanted area.

Therefore, it is desirable that an improved apparatus and method be provided for fusing opposing spinal vertebrae.

SUMMARY OF THE INVENTION

An embodiment of the present invention for a spinal implant includes a body assembly and a retention member coupled to the body assembly. The retention member includes a tang where the tang is extendible from the body assembly.

In a method of the present invention, the method includes the step of inserting an implant between adjacent vertebrae with a retention member of the implant in a first retracted configuration. The method also includes the step of configuring the retention member in a second extended configuration wherein when the retention member is in its second extended configuration, a portion of a tang of the retention member extends from the implant and into one of the adjacent vertebrae.

BRIEF DESCRIPTION OF THE DRAWINGS

The various features of the invention will best be appreciated by simultaneous reference to the description which follows and the accompanying drawings, in which:

FIG. 1 is a cross-sectional view of an embodiment of a spinal cage in a first configuration in accordance with the principles of the present invention;

FIG. 2 is a cross-sectional, partially exploded view of the spinal cage of FIG. 1 in a second configuration;

FIG. 14 is another side view of the retention member of FIG. 13;

DETAILED DESCRIPTION

Figures 1, 2:
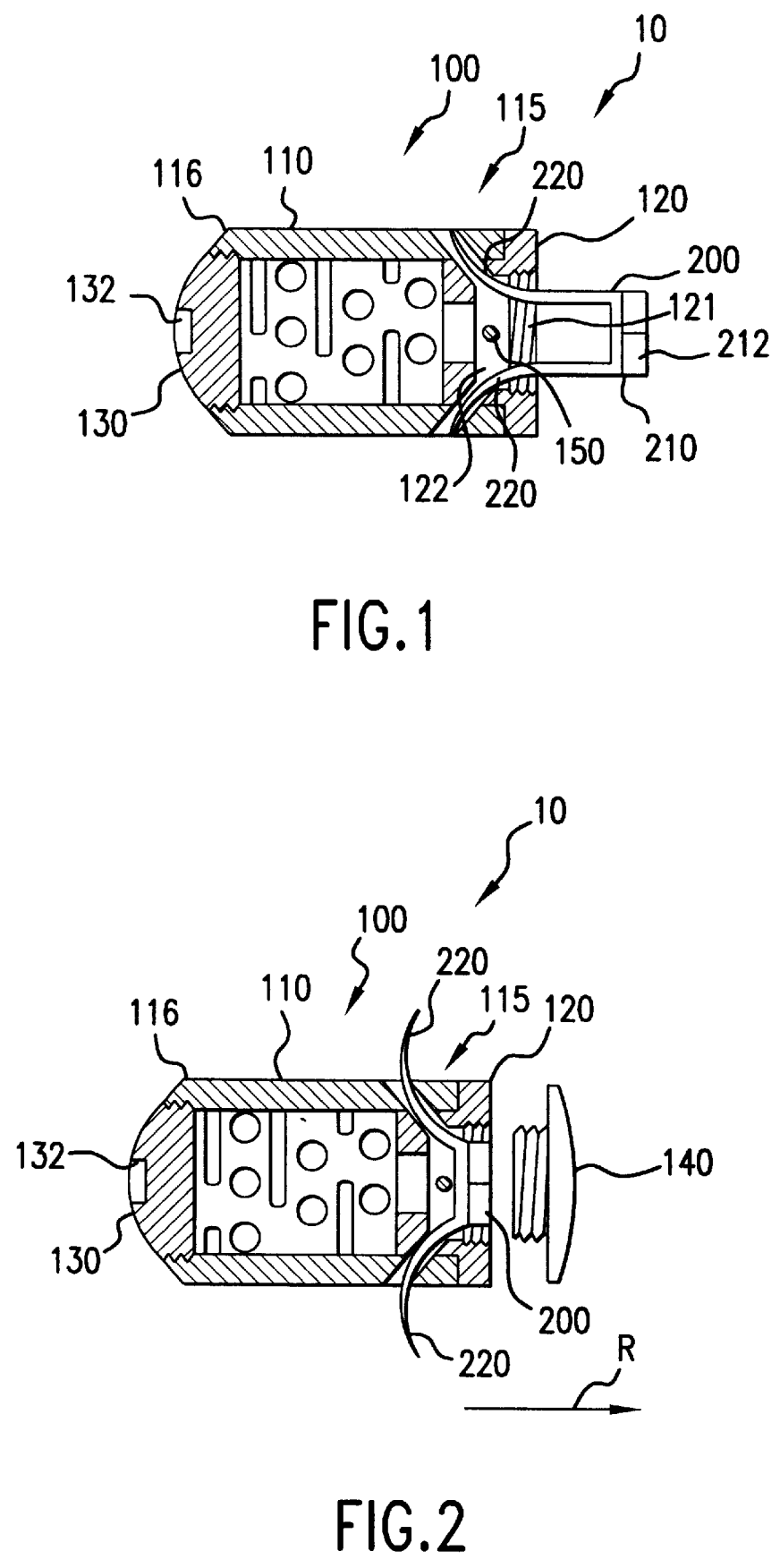
Figure 3:
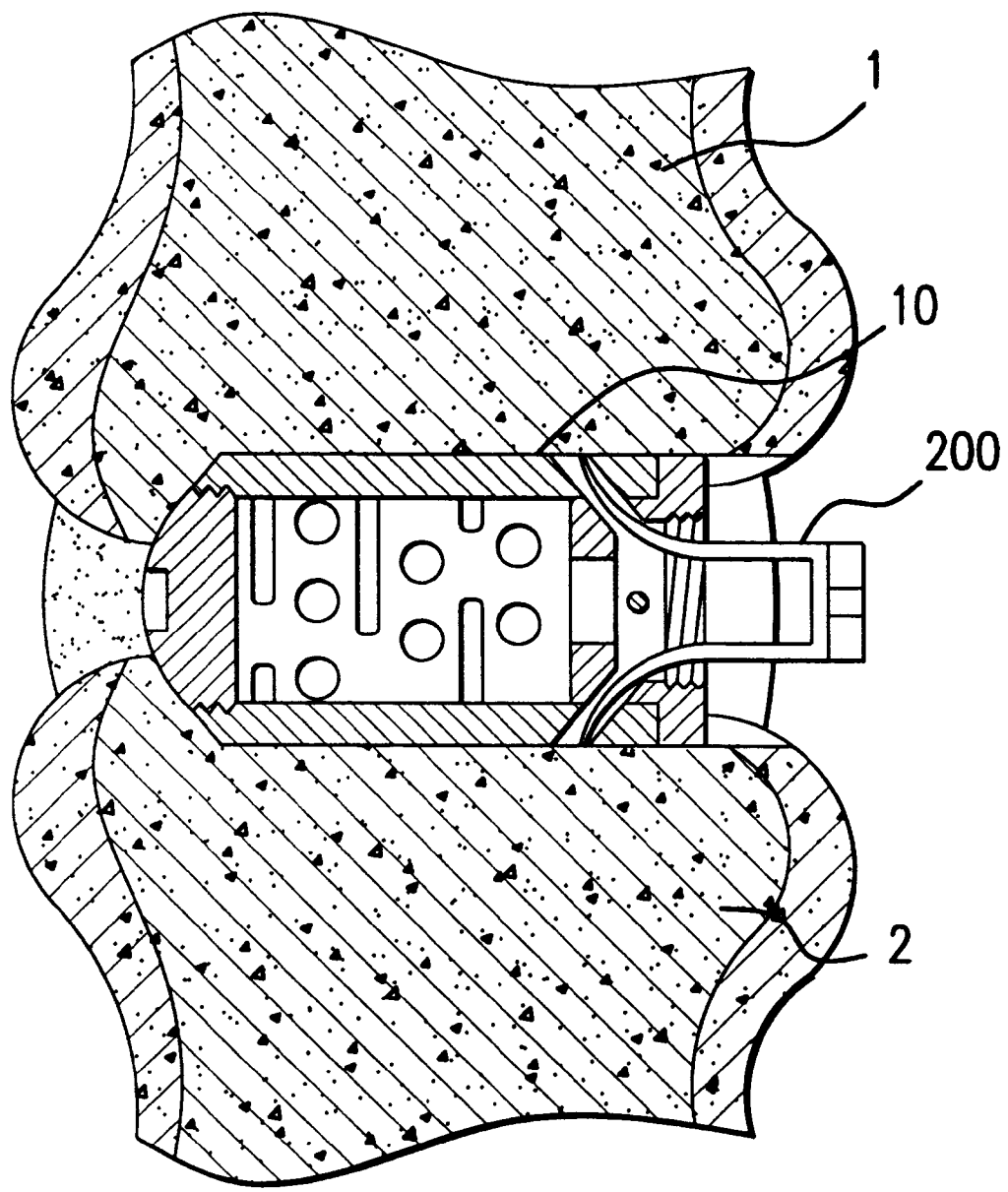
FIG. 3 illustrates the spinal cage between adjacent vertebrae in its first configuration.

An embodiment for the spinal cage 10 of the present invention is illustrated in FIGS. 1 and 2. As can be seen, and as will be described further later in this specification, the spinal cage 10 is comprised of a body assembly 100 and a retention member 200. Body assembly 100 is comprised of body 110 and end plug 120. Additionally, body assembly 100 may also include a distal end cap 130.

FIG. 1 illustrates the spinal cage 10 in a first configuration where the retention member 200 is not deployed from the body assembly 100. FIG. 2 illustrates the spinal cage 10 in a second configuration where the retention member 200 has been deployed from the body assembly 100 such that tangs 220 extend into surrounding bone structure of the patient.

Figure 4:
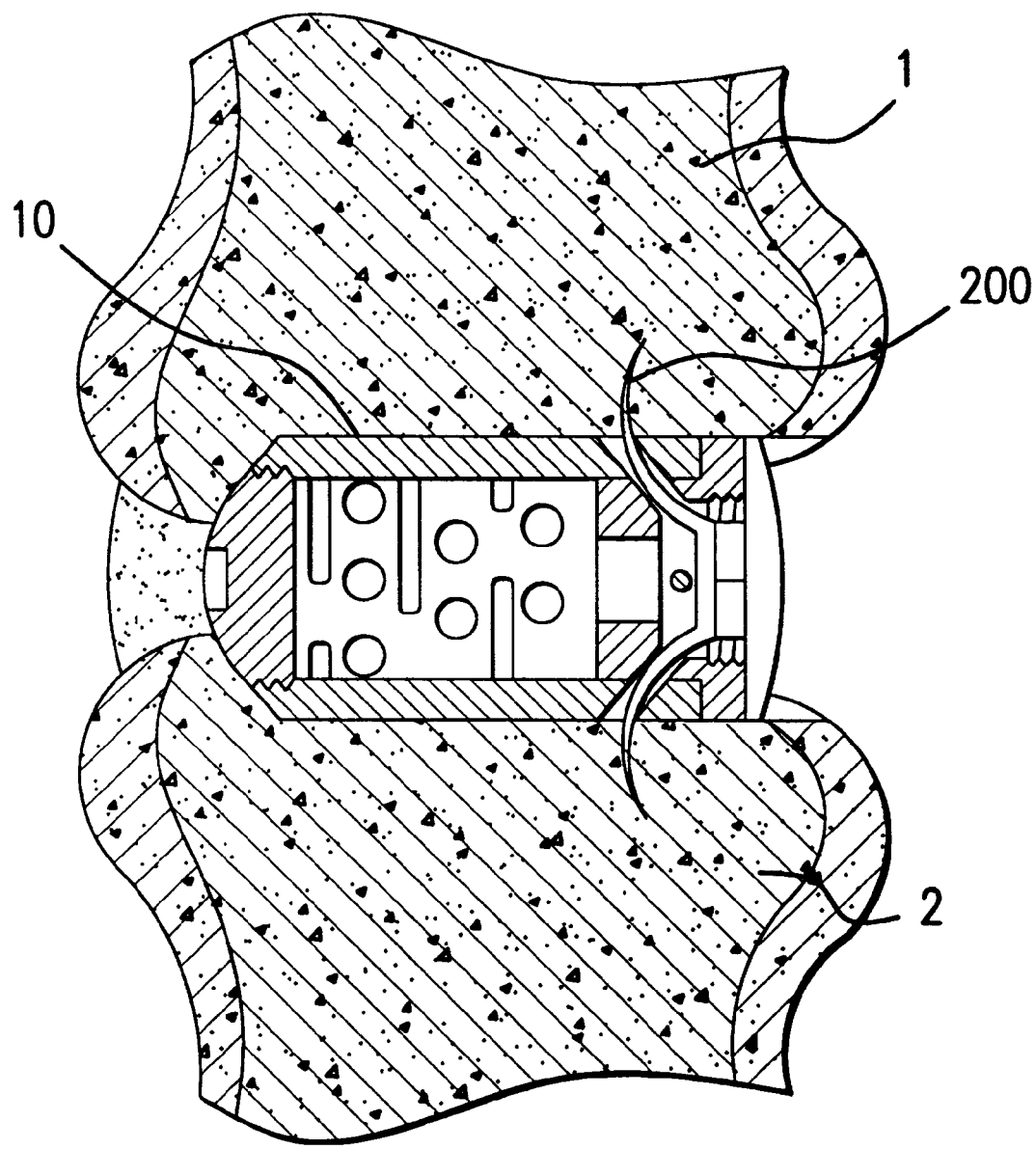
FIG. 4 illustrates the spinal cage between adjacent vertebrae in its second configuration.
Figure 5:
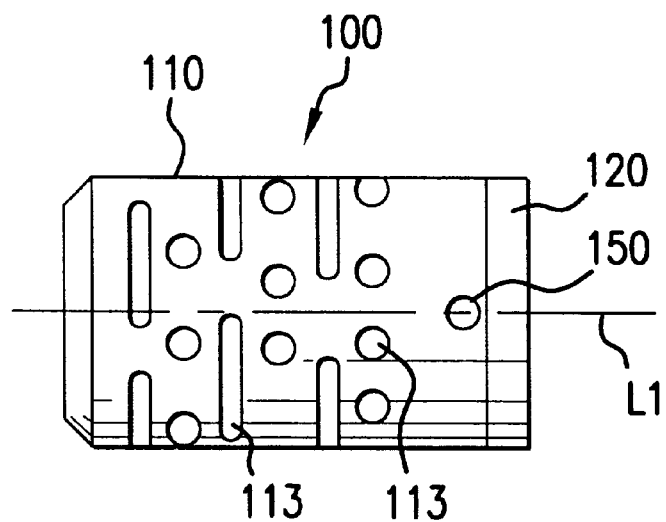
FIG. 5 is a side view of the body assembly of the spinal cage of FIG. 1.
Figure 6:
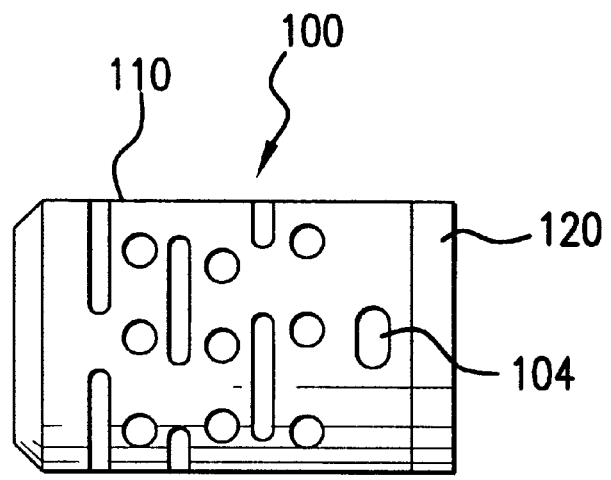
FIG. 6 is another side view of the body assembly of FIG. 5.
Figure 7:
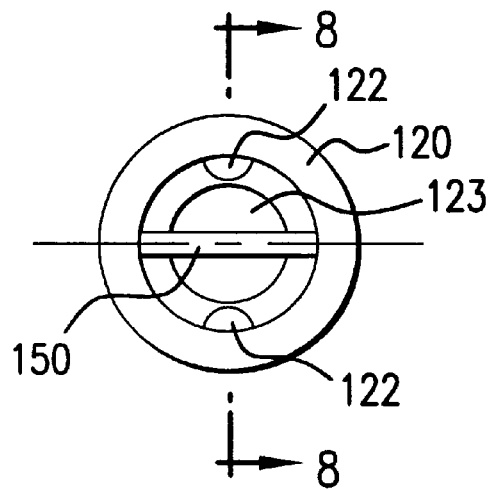
FIG. 7 is a top view of the body assembly of FIG. 5.

As can be seen in FIG. 3, when spinal cage 10 is in its first configuration retention member 200 is not deployed into bone portions 1 and 2. FIG. 4 illustrates spinal cage 10 in its second configuration where retention member 200 is deployed into bone portions 1 and 2.

Figure 17:
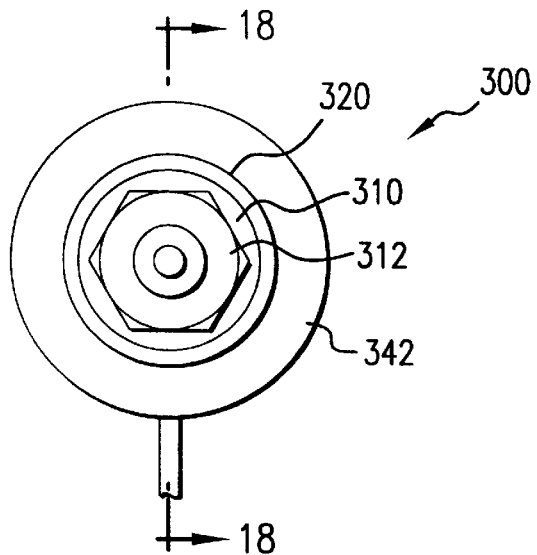
FIG. 17 is a top view of an embodiment of a deployment device that can be utilized in accordance with the principles of the present invention.
Figure 18:
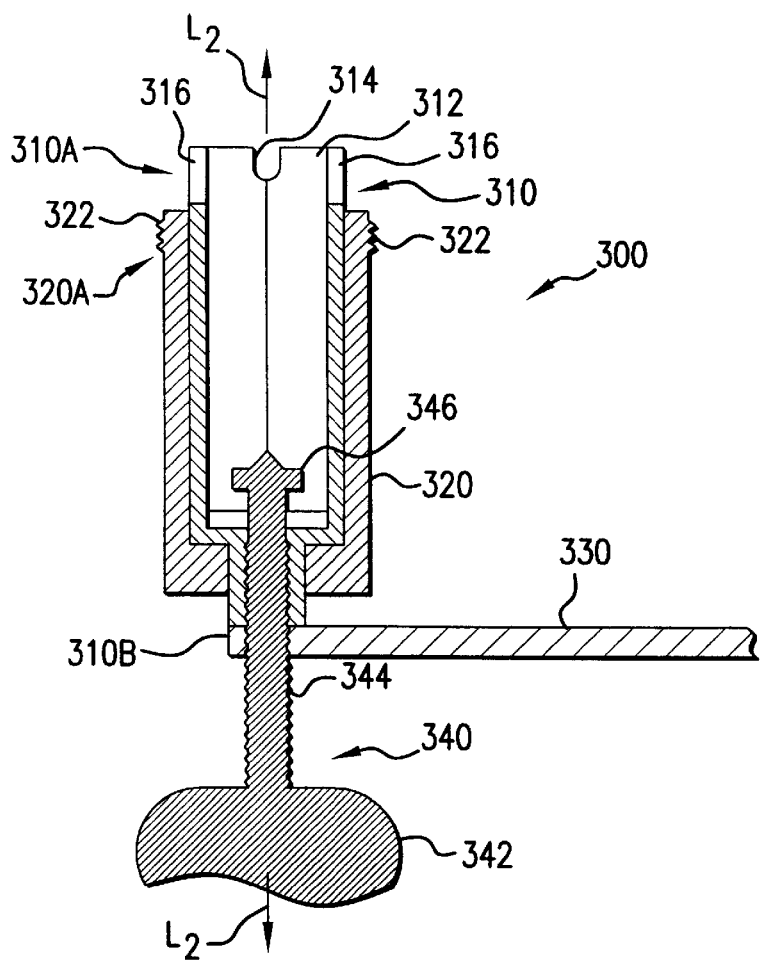
FIG. 18 is a cross-sectional view of the deployment device of FIG. 17 as taken along line 18—18 of FIG. 17.
Figure 19:
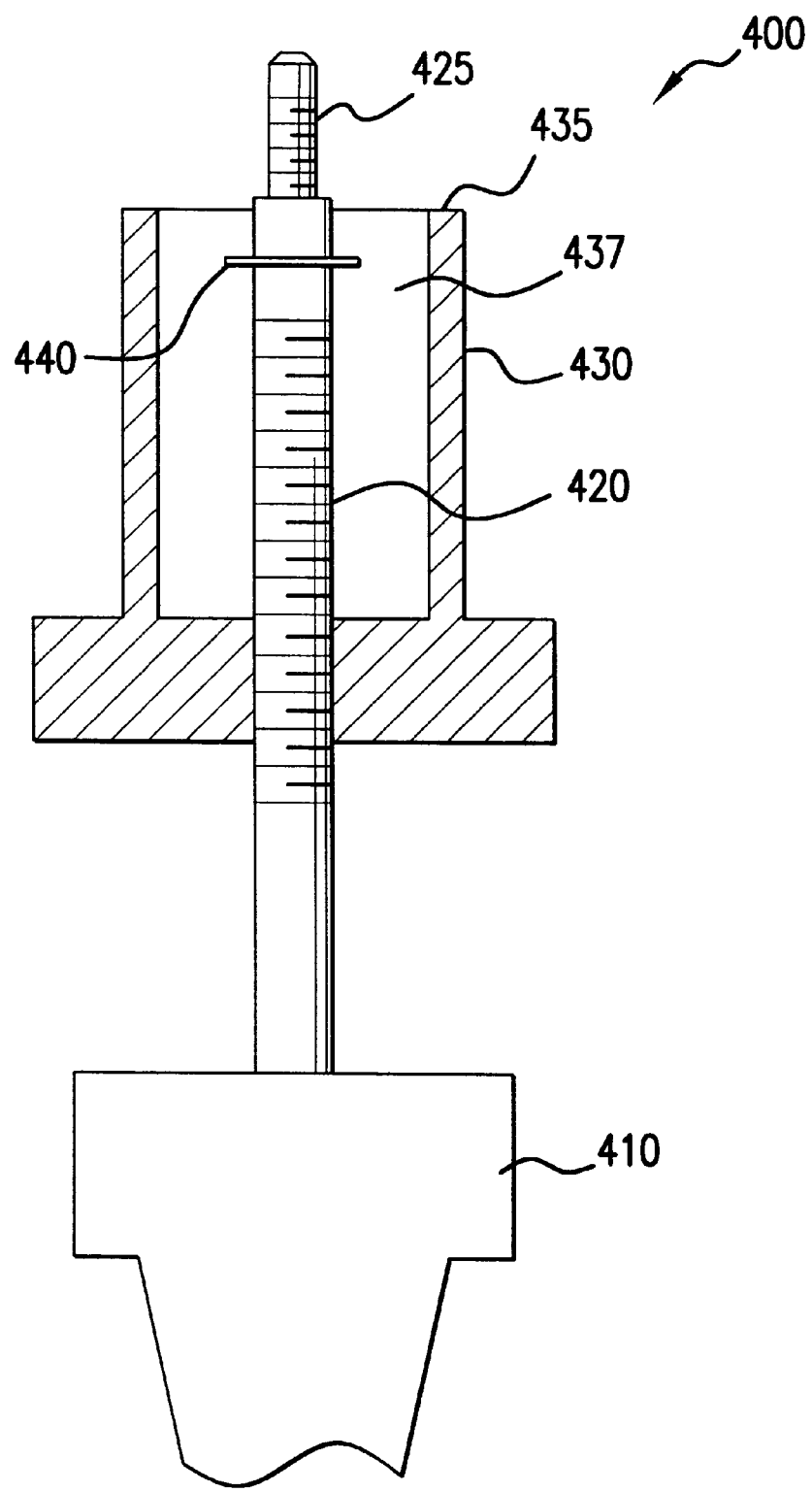
FIG. 19 is a partial cross-sectional view of an embodiment of a retraction device that can be utilized in accordance with the principles of the present invention.

As will also be further described later in this specification and as can be seen in FIGS. 17 and 18, a deployment device 300 is utilized to configure spinal cage 10 in its second configuration where tangs 220 are deployed from body assembly 100. A retraction device 400, as can be seen in FIG. 19, is utilized to return spinal cage 10 to its first configuration from its second configuration, where tangs 220 are returned to a position within body assembly 100.

Each of the above-described components and procedures will be described in further detail below.

As discussed above, spinal cage 10 includes body assembly 100. Body assembly 100 includes body 110, which in this embodiment is constructed of allograft cortical bone. In alternative embodiments, body 110 could be comprised of titanium alloy or a bioceramic material.

Figure 8:
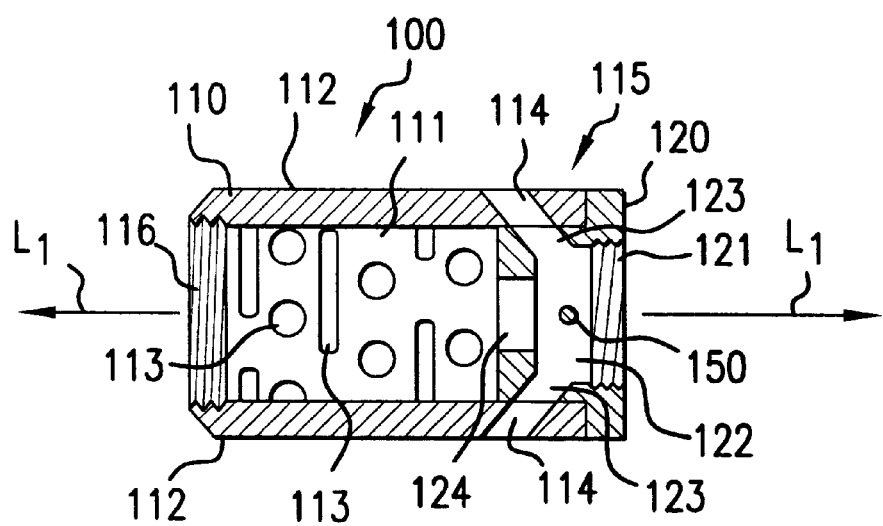
FIG. 8 is a cross-sectional view of the body assembly as taken along line 8—8 of FIG. 7.

As can be seen in FIG. 8, body 110 is a cylindrical member and includes a hollow bore 111 which extends therethrough. The interior of body 110 is hollow to allow it to be filled with a bone growth medium prior to implantation in the patient. The preferred bone growth medium is a cancellous bone cylindrical plug harvested from the patient. The cylindrical wall 112 of body 110, which defines bore 111, includes a plurality of ports 113 which extend completely through wall 112. Ports 113 may be formed in various configurations, including the circular and oval configurations illustrated. Ports 113 allow bone ingrowth, i.e., bone to grow from outside of body 110, and thus cylindrical wall 112, to within body 110 through ports 113.

Body 110 also includes two slots 114 which extend through wall 112. The two slots 114 are located on opposing sides of wall 112 and are oriented at an angle to the longitudinal axis $L_1$ of body cylinder 110. As will be explained, the tangs 220 of retention member 200 are received in, and are extendable through, slots 114.

As can be seen in FIGS. 1 and 2, distal end cap 130 is threadedly received within a distal portion of bore 111 at the distal end 116 of body 110. After a cancellous bone plug is inserted into the hollow interior, or bore 111, of body 110, end cap 130 is threaded into the internal threading included at distal end 116 of body 110. The end cap 130 is tightened by inserting a complementary-shaped tool into a square-formed slot 132 defined by end plug 130 and further threading end cap 130 into body 110.

End cap 130 utilizes a spherical radius on its exposed surface to prevent irritation to adjacent structures and, in its preferred embodiment, is constructed from a bioabsorbable material such as Poly-L-Lactic Acid (PLLA). End cap 130 will eventually be absorbed by the patient's body and will, thus, eventually leave the end of the cancellous bone plug inserted within body 110 exposed for further fusion to the patient's bone. An alternative material for comprising end cap 130 could be allograft cortical bone.

End plug 120 is received within a proximal portion of bore 111 at the proximal end 115 of body 110. End plug 120, in this embodiment, is comprised of stainless steel; however, other embodiments could be comprised of titanium alloy. In the preferred embodiment, the stainless steel end plug 120 is press-fitted into the allograft body cylinder 110. However, if titanium alloy is utilized for body 110, end plug 120 is integrally formed with body 110, i.e., its features are machined into body cylinder 110, and a single structure includes all of the features of body 110 and end plug 120.

If two structural components are utilized for end plug 120 and body 110, a stainless steel pin 150 is press-fitted through body cylinder 110 and end plug 120 to ensure the integrity of the assembly. Even if the body cylinder 110 and end plug 120 are integrally formed, the physical structure of pin 150 may be provided in the integral structure for purposes that will be discussed later.

End plug 120 contains internal threading 121 and a counterbore 122. Similar to body 110, end plug 120 also contains two slots 123. The two slots 123 are located on opposing sides of end plug 120 and are oriented at the same angle relative to the longitudinal axis $L_1$ of body cylinder 110 as are slots 114 of body 110. As will be explained, the tangs 220 of retention member 200 are received in, and are extendable through, the aligned slots 114 and 123 of the body 110 and end plug 120, respectively. The slots 114 and 123 are aligned during the process of assembling body 110 and end plug 120. The aligned slots are oriented 90 degrees from the longitudinal axis of pin 150.

FIGS. 9–12 illustrate a first embodiment for a retention member of the present invention. In this embodiment, retention member 200 is a one piece stainless steel structure consisting of a body 210, which defines a threaded hole 215 therein, and two tangs 220. The retention member 200 could also be constructed of titanium alloy or a combination of titanium alloy and nitinol if the other spinal cage components are of titanium alloy. In the embodiment of FIGS. 9–12, the retention member's tangs 220 have an oval cross-section and a rounded end at the distal tip 225 of each tang 220. As will be described later in this specification, and as can be seen in FIG. 2, the tangs 220 are deformable such that they are able to extend from body assembly 100 as retention member 200 is moved further into body assembly 100.

Figure 9:
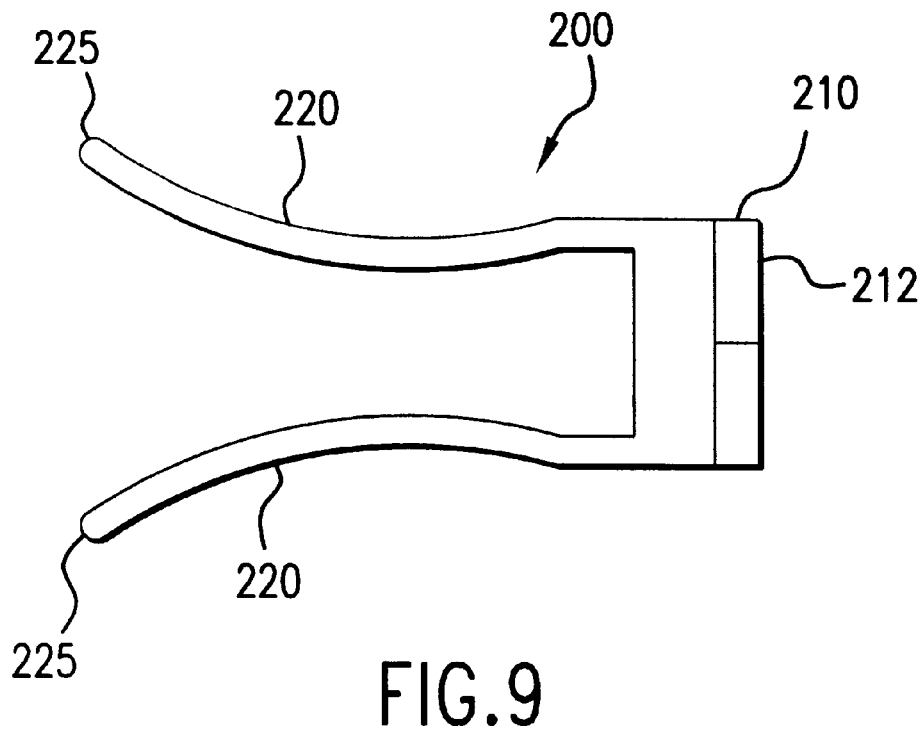
FIG. 9 is a side view of an embodiment of a retention member for the spinal cage in accordance with the principles of the present invention.
Figure 10:
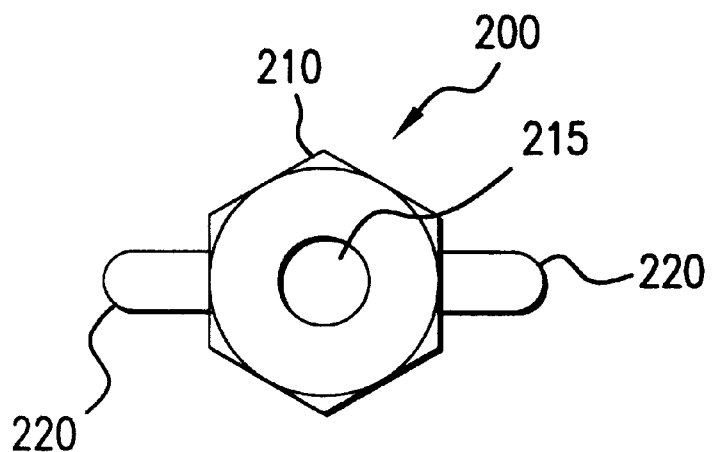
FIG. 10 is a top view of the retention member of FIG. 9.
Figure 11:
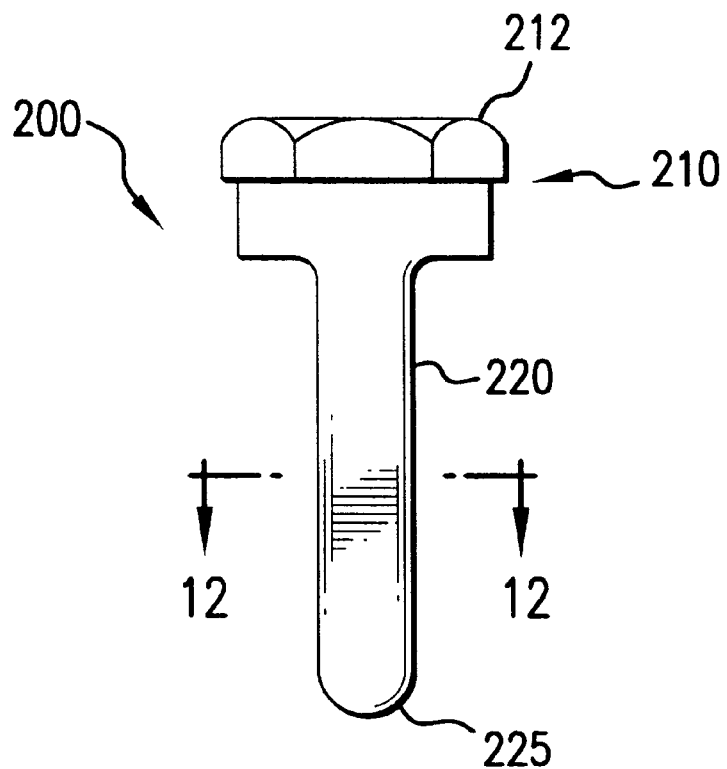
FIG. 11 is another side view of the retention member of FIG. 9.

Tangs 220 are pre-formed as illustrated in FIG. 9. Body 210 is cylindrical and includes a multi-faceted flange 212 at its proximal end, which is illustrated as being hexagonal in this embodiment. Threaded hole 215 extends through body 210 and, as will be further explained later in this specification, is utilized for reversing the deployment of retention member 200 from body assembly 100 in the event that the spinal cage must be removed from the patient.

Retention member 200 is pre-assembled into body assembly 100, as can be seen in FIG. 1. As can also be seen in FIG. 1, retention member 200 is assembled into body assembly 100 with tangs 220 fitted into the slots defined by the body assembly.

FIGS. 13–16 illustrate a second embodiment for a retention member of the present invention. Retention member 250 of this embodiment also includes a body 260, which defines a threaded hole 265 therein, and two tangs 270. As was body 210 of the previously discussed embodiment, body 260 is also cylindrical and includes a multi-faceted flange 262 at its proximal end, which is also hexagonal in this embodiment. However, the retention member 250 of this embodiment includes tangs 270 which have a triangular cross-section and a sharp end at the distal tip 275 of each tang 270. Retention member 270 may be comprised of the same materials as retention member 200.

A deployment device 300, as illustrated in FIGS. 17 and 18, is used to hold and insert the spinal cage 10 as well as to deploy the retention member 200, as will be explained later in this specification. Deployment device 300 includes a body 310 which has a multi-faceted bore 312 that is complementary in shape to the multi-faceted flange 212 of body 210 of retention member 200. In this embodiment, and as can be seen in FIG. 17, the bore 312 has a hexagonal shape. Multi-faceted flange 212 is slidably receivable within bore 312. Distal end 310A of body 310 includes an anti-rotation slot 314 and retention member tang slots 316. As will be explained, pin 150 is received within slot 314 and tangs 220 are received within slots 316.

Deployment device 300 also includes collar 320 which is free to rotate and translate about body 310 but is limited in translation by torque arm 330. Collar 320 contains external threads 322 at a distal end 320A of collar 320 which are threaded into the internal threads 121 of end plug 120 during use of deployment device 300. Torque arm 330 is attached to a proximal end 310B of body 310 and extends perpendicular to the longitudinal axis $L_2$ of body 310. A handle 340 includes a hand-grip portion 342 and an externally threaded shaft 344. The external threads of threaded shaft 344 threadedly engage with the internal threads included at the proximal end 310B of body 310. An anvil 346 is included at the distal end of shaft 344.

The use of spinal cage 10 and deployment device 300 will now be further described. The spinal cage is positioned such that the tangs 220 of retention member 200 are deployed parallel to the spinal axis. The deployment device 300 is keyed and marked to facilitate this orientation. The keying of the deployment device 300 is accomplished by slot 314 interfacing with pin 150. Since torque arm 330 is located 90° angularly with respect to slot 314 and torque arm 330 is marked "align parallel to spinal axis for fixation", the deployment device 300 is keyed and marked to assure that the tangs 220 deploy parallel to the spinal axis.

The deployment device 300 is fitted to the spinal cage 10 when the spinal cage is in its first configuration as shown in FIGS. 1 and 3. The body 310 of deployment device 300 is positioned over the protruding body 210 of retention member 200 such that the retention member body 210 is slidingly received within bore 312 of body 310 of deployment device 300. The complementary hexagonal shapes of bore 312 of deployment device 300 and flange 212 of body 210 of retention member 200 allow for easy alignment of deployment device 300 and retention member 200. The slots 316 of body 310 of deployment device 300 are aligned by the operator with the retention member tangs 220 such that, as body 310 of deployment device 300 is pushed into counterbore 122 of end plug 120, the tangs 220 are received within the slots 316; this in-turn will the align anti-rotation slot 314 of body 310 with pin 150 of body assembly 100. Insertion of pin 150 within slots 314 will prevent rotation of body 310.

Collar 320, which contains external threading 322 at a distal end 320A thereof, is threaded into the internal threads 121 of end plug 120. Body 310 of deployment device 300 is now captivated and restrained against further translation by collar 320 and restrained against further rotation by pin 150.

When torque arm 330 is held parallel to the spinal axis, which is aligned perpendicular with the longitudinal axes of the body assembly 100 and deployment device 300, the retention member's tangs 220 will deploy parallel to the spinal axis. To deploy the tangs 220, the torque arm 330, which is part of body 310, is held with one hand of the operator and handle 340 is rotated clockwise with the operator's other hand. As handle 340 is rotated, the external threads on shaft 344 interact with the internal threads of body 310 at the proximal end 310B of body 310 to cause anvil 346 to progress towards the distal end 310A of body 310 and engage with body 210 of retention member 200. Further distal movement of anvil 346 causes retention member 200 to move distally towards the interior of the body assembly 100 which inturn forces tangs 220 out through the aligned slots 114 of body 110 and slots 123 of end plug 120, and thus out through body assembly 100 and into the cancellous bone of the vertebra. This process is continued until the retention member body 210 engages with pin 150.

Tangs 220 are deformable such that, as they are forced out of body assembly 100 through the aligned slots 114, 123, they engage with the walls that define the slots. Further distal movement of the tangs 220 through the slots deform the tangs as they are pushed through the slots and extended from body assembly 100.

It can be understood that during deployment of the retention member 200, because the faceted body 210 of the retention member, e.g., the hexagonal shape, was slidingly received in the complementary-formed faceted bore 312 of the deployment device body 310, rotation of the retention member body 210 was prevented thus ensuring against any twisting or bending of the retention member tangs 220 during their deployment.

FIGS. 2 and 4 illustrate the spinal cage 10 in its second configuration where it is fully deployed into cancellous bone within the cortical bone of the vertebra and the implant is restrained from translation or rotation. Collar 320 is then unthreaded from the spinal cage 10, and more specifically from end plug 120, and the deployment device 300 is removed.

Figure 12:
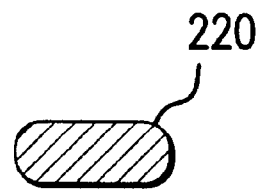
FIG. 12 is a cross-sectional view of a tang of the retention member of FIG. 9 as taken along line 12—12 of FIG. 11.
Figure 13:
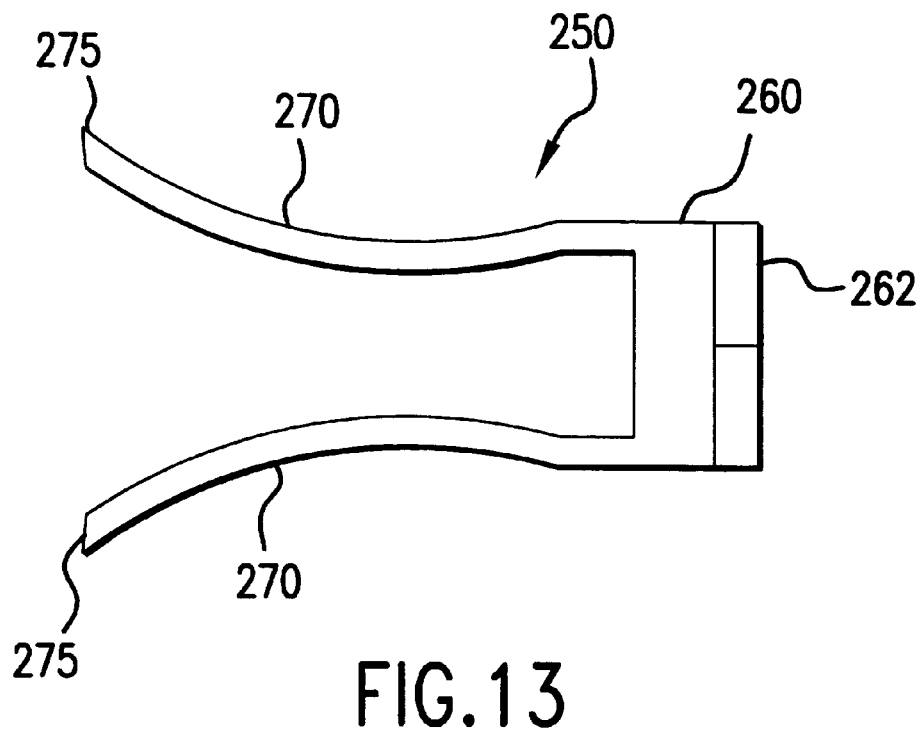
FIG. 13 is a side view of a second embodiment of a retention member for the spinal cage in accordance with the principles of the present invention.
Figure 14:
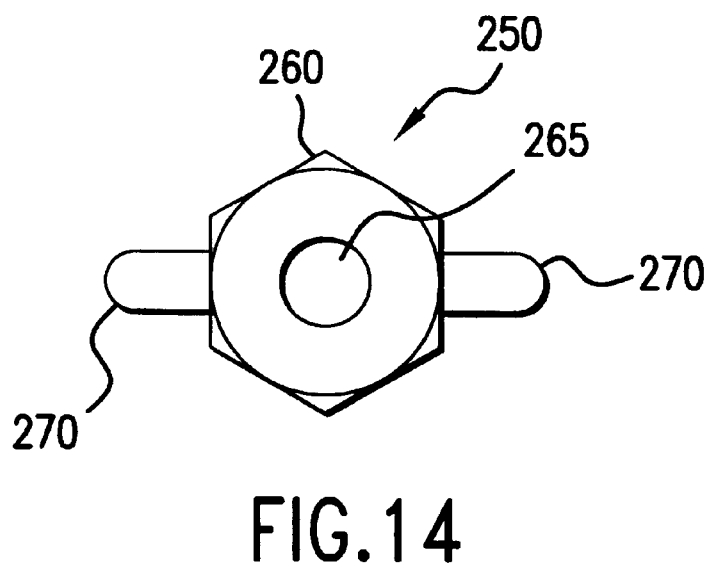
FIG. 14 is a top view of the retention member of FIG. 13.
Figure 15:
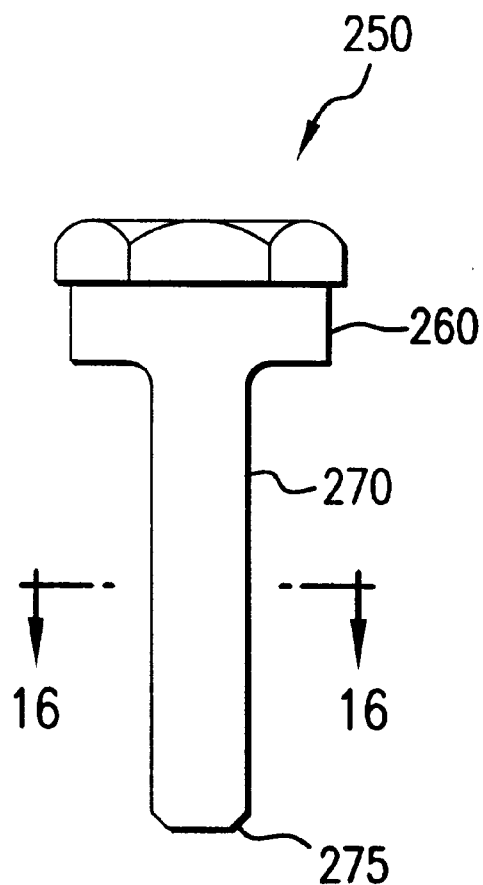
Figure 16:
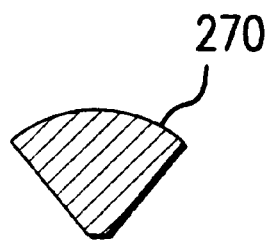
FIG. 16 is a cross-sectional view of a tang of the retention member of FIG. 13 as taken along line 16—16 of FIG. 15.

After removal of the deployment device 300, proximal end cap 140, as can be seen in FIG. 2, is threaded into the threaded hole of the retention member's body, e.g., hole 215 of body 210 for the embodiment of retention member 200 of FIGS. 9 12. End cap 140 is utilized to close the trailing end of the spinal cage 10 and avoid irritation to adjacent structures. The exposed surface of end cap 140 has a spherical radius and contains an internal square drive feature, similar to square-formed slot 132 for distal end cap 130, for use in tightening the proximal end cap 140 in retention member 200. The threads of end cap 140 are slightly oversized to provide a self-locking feature and prevent inadvertent loosening of the end cap from the retention member. The preferred embodiment of end cap 140 is constructed from Ultra High Molecular Weight Polyethylene (UHMWPE) material. These threads, and end cap 140 as a whole, also prevent any ingrowth into the threaded hole of the retention member to make future removal of the retention member easier, if necessary for any reason.

The retention member's deployment of tangs 220 can be reversed, if necessary, for removal of the spinal cage 10. In order to retract the tangs 220, the retraction device 400, as shown in FIG. 19, is used. Retraction device 400 includes a handle 410, an externally threaded shaft 420, which has a threaded stem 425 on a distal end thereof, and a collar 430. Threaded shaft 420, and thus threaded stem 425, are rigidly attached to handle 410. Collar 430 is threadedly engaged with threaded shaft 420. A snap-ring 440 may be included on shaft 420 to prevent collar 430 from being inadvertently threaded off of shaft 420.

To retract tangs 220, end cap 140 is first unthreaded, and thus removed, from retention member 200. The user then uses retraction device 400 to retract the tangs. The user holds handle 410 and turns it so as to engage threaded stem 425 into the threaded hole of the body of the retention member, e.g., hole 215 of body 210. When threaded stem 425 is fully engaged in threaded hole 215, handle 410 is restrained against further rotation and collar 430 is rotated clockwise to thread it distally on threaded shaft 420, causing it to advance toward the spinal cage 10 due to interaction of the collar's internal threading with the shaft's external threading. As stated above, snap ring 440 prevents collar 430 from being inadvertently removed from shaft 420. As collar 430 advances toward the spinal cage 10, its leading edge 435 will contact the end plug 120. Further rotation of collar 430 on shaft 420, and the contact between collar 430 and end plug 120, will cause a reaction force on the retention member 200 and will move retention member 200 in the direction R as shown in FIG. 2. The movement of retention member 200 in this direction will retract tangs 220 from extending outside of body assembly 100 and force the tangs back through slots 114, 123. Further movement of retention member 200 in direction R will pull it from body assembly 100 and into the open area 437 within collar 430. Through the above-described procedure, the spinal cage 10 can now be removed from the patient's body.

Whereas the above description discussed use of the embodiment of FIGS. 9–12 for the retention member, it is understood that alternative embodiments for the retention member, including the alternative embodiment illustrated in FIGS. 13–16, can be utilized in the present invention.

Figure 20:
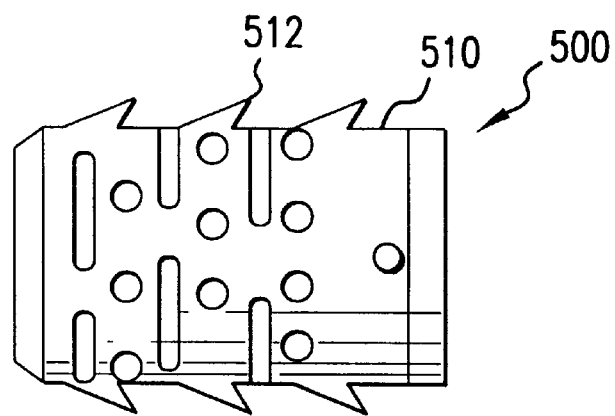
FIG. 20 is a side view of an alternative embodiment of a body assembly in accordance with the principles of the present invention.
Figure 21:
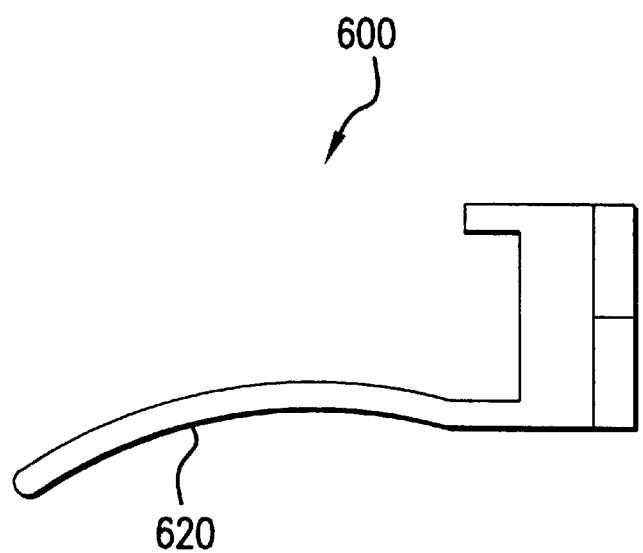
FIG. 21 is a side view of another alternative embodiment of a retention member for the spinal cage in accordance with the principles of the present invention.

The disclosed embodiments are illustrative of the various ways in which the present invention may be practiced. Other embodiments can be implemented by those skilled in the art without departing from the spirit and scope of the present invention. For example, external threading 512 may be included on a body 510 of a body assembly 500, as is illustrated in FIG. 20, to further enhance the fusing of the adjacent vertebrae. Additionally, whereas the retention member is illustrated as including two tangs, the present invention may be practiced by only including one tang on the retention member. FIG. 21 illustrates an alternative embodiment for a retention member 600 that only includes one tang 620. All of the other features of retention member 600 are similar to those as described for the embodiments of retention members 200 and 250.

What is claimed is:

1. A spinal implant, comprising:
   a body assembly; and
   a retention member coupled to the body assembly, the retention member including a body, a multi-faceted flange attached to a proximal end of the body, and a first tang extendible through the body assembly.

2. The spinal implant of claim 1 wherein the retention member includes:
   a second tang, wherein the first tang and the second tang extend from a distal end of the body.

3. The spinal implant of claim 2 wherein the first and second tangs are formed of a deformable material.

4. The spinal implant of claim 3 wherein the first and second tangs are extendible though slots included in the body assembly.

5. The spinal implant of claim 1 wherein the body assembly includes:
   a body, the body including a cylindrical wall defining a bore and the cylindrical wall defining a plurality of apertures extending therethrough; and
   an end plug, the end plug coupled to the body.

6. The spinal implant of claim 5 wherein the end plug includes an internally threaded portion and a counterbore.

7. The spinal implant of claim 5 further comprising a pin, the pin received through the body and the end plug.

8. The spinal implant of claim 5 wherein the body assembly further includes a distal end cap coupled to a distal end of the body.

9. In combination with the spinal implant of claim 1, a deployment device couplable to the spinal implant, the deployment device including:
   a body defining a bore, the retention member slidably receivable within the bore;
   a collar rotatable and translational about the body;
   a torque arm attached to a proximal end of the body and extending perpendicular to a longitudinal axis of the body; and
   a handle extending through the proximal end of the body and within the bore.

10. The deployment device of claim 9 wherein the handle includes:
    a hand-grip portion;
    an externally threaded shaft attached to the hand-grip portion; and
    an anvil attached to a distal end of the externally threaded shaft and disposed within the bore.

11. In combination with the spinal implant of claim 1, a retraction device couplable to the spinal implant, the retraction device including:
    a collar defining a bore, the retention member slidably receivable within the bore;
    an externally threaded shaft, the shaft threadedly engaged with the collar and including a threaded stem on a distal end thereof; and
    a handle rigidly attached to the externally threaded shaft.

12. The retraction device of claim 11 further comprising a snap-ring disposed on the externally threaded shaft and within the bore.

13. The implant of claim 1, wherein said body defines a threaded aperture therein.

14. An implant, comprising:
    a body assembly; and
    a retention member including a body, a multi-faceted flange attached to a proximal end of the body, and a tang, the retention member receivable within the body assembly;
    wherein when the retention member is in a first configuration, the tang is retracted within the body assembly and wherein when the retention member is in a second configuration, a portion of the tang is extended through the body assembly.

15. The implant of claim 13 wherein the tang is comprised of a deformable material.

16. The implant of claim 13 wherein the body assembly includes:
    a body, the body including a cylindrical wall defining a bore and the cylindrical wall defining a plurality of apertures extending therethrough; and
    an end plug, the end plug coupled to the body.

17. The implant of claim 15 further comprising a pin, the pin received through the body and the end plug.

18. The implant of claim 15 wherein the body includes threading on an external surface thereof.

19. A method of fusing adjacent vertebrae comprising the steps of:
    inserting an implant between the adjacent vertebrae with a retention member of the implant in a first retracted configuration; and
    configuring the retention member in a second extended configuration wherein when the retention member is in its second extended configuration, a portion of a tang of the retention member extends from the implant and into one of the adjacent vertebrae.

20. The method of claim 18 wherein when the retention member is in its second extended configuration, a portion of a second tang of the retention member extends from the implant and into the other of the adjacent vertebrae.

21. The method of claim 19 wherein the step of configuring the retention member in the second extended configuration includes the step of deforming the first and second tangs.

* * * * *